(12) United States Patent
Barker et al.

(10) Patent No.: US 10,759,744 B2
(45) Date of Patent: Sep. 1, 2020

(54) PROCESS FOR THE PRODUCTION OF FORMALDEHYDE-STABILIZED UREA

(71) Applicant: JOHNSON MATTHEY PUBLIC LIMITED COMPANY, London (GB)

(72) Inventors: Sam Barker, Billingham (GB); Thomas Davison, Billingham (GB); John David Pach, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/500,441

(22) PCT Filed: Mar. 22, 2018

(86) PCT No.: PCT/GB2018/050747
§ 371 (c)(1),
(2) Date: Oct. 3, 2019

(87) PCT Pub. No.: WO2018/185459
PCT Pub. Date: Oct. 11, 2018

(65) Prior Publication Data
US 2020/0109108 A1    Apr. 9, 2020

(30) Foreign Application Priority Data

Apr. 5, 2017   (GB) .................................. 1705487.5

(51) Int. Cl.
| | | |
|---|---|---|
| C07C 273/02 | (2006.01) | |
| C07C 29/151 | (2006.01) | |
| C01C 1/04 | (2006.01) | |
| C07C 45/38 | (2006.01) | |
| C01B 3/34 | (2006.01) | |

(52) U.S. Cl.
CPC ............ *C07C 273/025* (2013.01); *C01B 3/34* (2013.01); *C01C 1/04* (2013.01); *C07C 29/151* (2013.01); *C07C 45/38* (2013.01); *C01B 2203/0233* (2013.01); *C01B 2203/0283* (2013.01); *C01B 2203/0475* (2013.01); *C01B 2203/061* (2013.01); *C01B 2203/068* (2013.01); *C01B 2203/1235* (2013.01)

(58) Field of Classification Search
CPC ... C07C 273/025; C07C 29/151; C07C 45/38; C01B 3/34; C01C 1/04
USPC .......................................................... 564/69
See application file for complete search history.

(56) References Cited

U.S. PATENT DOCUMENTS

| | | | |
|---|---|---|---|
| 9,085,513 B2 | 7/2015 | Dahl | |
| 10,077,235 B2* | 9/2018 | Erlandsson | C07C 45/29 |
| 10,087,140 B2* | 10/2018 | Erlandsson | C01C 1/0488 |
| 10,479,761 B2* | 11/2019 | Davison | C07C 29/1518 |
| 2012/0247104 A1 | 10/2012 | Handagama et al. | |

FOREIGN PATENT DOCUMENTS

| | | |
|---|---|---|
| EP | 2896596 A1 | 7/2015 |
| GB | 2539294 A | 12/2016 |
| GB | 2539521 A | 12/2016 |
| JP | 5863979 B2 | 12/2016 |
| WO | 2014122894 A1 | 8/2014 |
| WO | 2016132091 A1 | 8/2016 |
| WO | 2016132092 A1 | 8/2016 |

OTHER PUBLICATIONS

PCT/GB2018/050747 International Search Report dated Jun. 13, 2018.
PCT/GB2018/050747 Written Opinion dated Jun. 13, 2018.
GB1705487.5 Search Report dated Feb. 15, 2018.
GB1804565.8 Search Report dated Nov. 8, 2018.
Magnusson, et al., "UFC Manufacture for Urea Production", Nitrogen + Syngas 2016 International Conference, Berlin, Feb. 29-Mar. 3, 2016, p. 97-106.
Søgaard-Andersen, et al., "Methanolation in Ammonia Plants", AIChE Ammonia Plant Safety Symposium, 1991. Aiche 32-19 p. 177-186.
Shields, et al. "Coproduction of Ammonia and Methanol", AIChE Ammonia Plant Safety Symposium, 1996. Aiche 36-026 p. 259-267.

* cited by examiner

*Primary Examiner* — Yong L Chu
(74) *Attorney, Agent, or Firm* — BakerHostetler (57) ABSTRACT

A process for the production of formaldehyde-stabilised urea is described comprising the steps of: (a) generating a synthesis gas; (b) subjecting the synthesis gas to one or more stages of water-gas shift in one or more water-gas shift reactors to form a shifted gas; (c) cooling the shifted gas to below the dew point and recovering condensate to form a dried shifted gas; (d) recovering carbon dioxide from the dried shifted gas in a carbon dioxide removal unit to form a carbon dioxide-depleted synthesis gas; (e) synthesising methanol from the carbon dioxide-depleted synthesis gas in a methanol synthesis unit and recovering the methanol and a methanol synthesis off-gas; (f) subjecting at least a portion of the recovered methanol to oxidation with air to form formaldehyde in a stabiliser production unit; (g) subjecting the methanol synthesis off-gas to methanation in a methanation reactor containing a methanation catalyst to form an ammonia synthesis gas; (h) synthesising ammonia from the ammonia synthesis gas in an ammonia production unit and recovering the ammonia; (i) reacting a portion of the ammonia and at least a portion of the recovered carbon dioxide stream in a urea production unit to form a urea stream; and (j) stabilising the urea by mixing the urea stream and a stabiliser prepared using the formaldehyde produced in the stabiliser production unit, wherein the carbon dioxide removal unit operates by means of absorption using a liquid absorbent and comprises an absorbent regeneration unit, wherein the process includes recovering a carbon dioxide-containing gas stream from the absorbent regeneration unit, compressing at least a portion of the recovered carbon dioxide-containing gas stream to form a compressed carbon dioxide-containing gas stream and passing the compressed carbon dioxide-containing gas stream to the methanol synthesis unit.

20 Claims, 1 Drawing Sheet

PROCESS FOR THE PRODUCTION OF FORMALDEHYDE-STABILIZED UREA

CROSS-REFERENCE TO RELATED APPLICATIONS

This application is the National Stage of International Patent Application No. PCT/GB2018/050747, filed Mar. 22, 2018, which claims priority to Great Britain Patent Application No. 1705487.5 filed Apr. 5, 2017, the entire disclosures of both of which are incorporated herein by reference for any and all purposes.

The present invention relates to a process for the production of stabilised urea. More particularly, it relates to an integrated process for the production of formaldehyde-stabilised urea in a process including the co-production of methanol and ammonia.

Urea finds widespread use as a fertiliser and in industrial chemical manufacture. It is conventionally made by reacting ammonia with carbon dioxide to form a solid product which is often shaped by prilling or granulating. Aqueous formaldehyde or a urea-formaldehyde concentrate (UFC) are often used to stabilise the urea before or during the shaping process.

However, the demand for formaldehyde to produce stabilised urea from a single production facility is small and normally beyond the economic feasibility for a dedicated formaldehyde production facility. Due to the small scale of the requirements, the formaldehyde is normally produced at a separate dedicated formaldehyde production facility and transported to the ammonia/urea production facility where it is stored.

WO2016/132092 and WO2016/132091 disclose integrated processes for the production of formaldehyde-stabilised urea in which methanol used in formaldehyde production is synthesised from a carbon dioxide-depleted synthesis gas recovered from a carbon-dioxide removal unit.

In some instances, it may be necessary to produce more methanol and thereby more formaldehyde stabiliser than is required in a single urea production facility, for examples to feed multiple urea plants. When this is the case, or if there is insufficient carbon oxides in the synthesis gas outlet of the carbon dioxide removal unit to generate the required formaldehyde stabiliser, there is a need to provide a suitable synthesis gas to increase methanol production and thereby the formaldehyde stabiliser production, We have developed an integrated urea production process with a dedicated formaldehyde stabiliser production unit based on a methanol-ammonia co-production process that improves the overall efficiency and flexibility of the prior art processes.

Accordingly the invention provides a process for the production of formaldehyde-stabilised urea comprising the steps of: (a) generating a synthesis gas comprising hydrogen, nitrogen, carbon monoxide, carbon dioxide and steam in a synthesis gas generation unit; (b) subjecting the synthesis gas to one or more stages of water-gas shift in one or more water-gas shift reactors to form a shifted gas; (c) cooling the shifted gas to below the dew point and recovering condensate to form a dried shifted gas; (d) recovering carbon dioxide from the dried shifted gas in a carbon dioxide removal unit to form a carbon dioxide-depleted synthesis gas; (e) synthesising methanol from the carbon dioxide-depleted synthesis gas in a methanol synthesis unit and recovering the methanol and a methanol synthesis off-gas comprising nitrogen, hydrogen and residual carbon monoxide; (f) subjecting at least a portion of the recovered methanol to oxidation with air to form formaldehyde in a stabiliser production unit; (g) subjecting the methanol synthesis off-gas to methanation in a methanation reactor containing a methanation catalyst to form an ammonia synthesis gas; (h) synthesising ammonia from the ammonia synthesis gas in an ammonia production unit and recovering the ammonia; (i) reacting a portion of the ammonia and at least a portion of the recovered carbon dioxide stream in a urea production unit to form a urea stream; and (j) stabilising the urea by mixing the urea stream and a stabiliser prepared using the formaldehyde produced in the stabiliser production unit, wherein the carbon dioxide removal unit operates by means of absorption using a liquid absorbent and comprises an absorbent regeneration unit, wherein the process includes recovering a carbon dioxide-containing gas stream from the absorbent regeneration unit, compressing a portion of the recovered carbon dioxide gas steam to form a compressed carbon dioxide-containing gas stream and passing the compressed carbon dioxide-containing gas stream to the methanol synthesis unit.

The synthesis gas comprising carbon monoxide, carbon dioxide, hydrogen and nitrogen provided in step (a) may be formed by any suitable means. Different synthesis gas generation units can provide synthesis gases with different carbon monoxide:carbon dioxide ratios. The process allows the product mix to be adjusted for a wide range of synthesis gas compositions. The synthesis gas generation may comprise primary steam reforming of a preferably desulphurised hydrocarbon, such as natural gas, naphtha or a refinery off-gas, and secondary reforming of the resulting primary reformed gas with air or oxygen-enriched air; or by the gasification of a carbonaceous feedstock, such as coal or biomass with air. Preferably the synthesis gas generation stage comprises steam reforming a hydrocarbon. This may be achieved by primary reforming a hydrocarbon with steam in externally-heated catalyst-filled tubes in a fired- and/or gas-heated steam reformer and secondary reforming the primary-reformed gas in an autothermal or secondary reformer by subjecting it to partial combustion with air, or air enriched in oxygen, and then passing the partially combusted gas mixture through a bed of steam reforming catalyst. A heat exchange reformer, such as a gas-heated steam reformer (GHR), may be operated in parallel with a conventional fired reformer or in series with a conventional fired reformer and the product gas fed to a common secondary reformer. By-passing a portion of the hydrocarbon feedstock around a primary reformer may be used to reduce the carbon monoxide:carbon dioxide ratio in the synthesis gas. If desired one or more stages of adiabatic pre-reforming may also be performed before the fired reformer and/or heat exchange reformer.

The primary reforming catalyst typically comprises nickel at levels in the range 5-30% wt, supported on shaped refractory oxides, such as alpha alumina, magnesium aluminate or calcium aluminate. If desired, catalysts with different nickel contents may be used in different parts of the tubes, for example catalysts with nickel contents in the range 5-15% wt or 30-85% wt may be used advantageously at inlet or exit portions of the tubes. Alternatively, structured catalysts, wherein a nickel or precious metal catalyst is provided as a coated layer on a formed metal or ceramic structure may be used, or the catalysts may be provided in a plurality of containers disposed within the tubes. Steam reforming reactions take place in the tubes over the steam reforming catalyst at temperatures above 350° C. and typically the process fluid exiting the tubes is at a temperature in the range 650-950° C. The heat exchange medium flowing around the outside of the tubes may have a temperature in the range 800-1300° C. In a GHR the catalyst temperatures are above 350° C. and typically the process fluid exiting the tubes is at a temperature in the range 500-950° C. and the heat exchange medium flowing around the outside of the tubes may have a temperature in the range 500-1200° C. The pressure may be in the range 10-80 bar abs. In a secondary reformer, the primary-reformed gas is partially combusted often in a burner apparatus mounted usually near the top of the reformer. The partially combusted reformed gas is then passed adiabatically through a bed of a steam reforming catalyst usually disposed below the burner apparatus, to bring the gas composition towards equilibrium. Heat for the endothermic steam reforming reaction is supplied by the hot, partially combusted reformed gas. As the partially combusted reformed gas contacts the steam reforming catalyst it is cooled by the endothermic steam reforming reaction to temperatures in the range 800-1100° C. The bed of steam reforming catalyst in the secondary reformer typically comprises nickel at levels in the range 5-30% wt, supported on shaped refractory oxides, but layered beds may be used wherein the uppermost catalyst layer comprises a precious metal, such as platinum or rhodium, on a zirconia support. Such steam reforming apparatus and catalysts are commercially available.

Alternatively, the steam reforming may be achieved by passing a mixture of the hydrocarbon and steam through an adiabatic pre-reformer containing a bed of steam reforming catalyst and then passing the pre-reformed gas mixture and air to an autothermal reformer which operates in the same way as the secondary reformer to produce a gas stream containing hydrogen, carbon oxides and steam. In adiabatic pre-reforming, a mixture of hydrocarbon and steam, typically at a steam to carbon ratio in the range 1-4, is passed at an inlet temperature in the range 300-620° C. to a fixed bed of pelleted nickel-containing pre-reforming catalyst. Such catalysts typically comprise 40% wt nickel (expressed as NiO) and may be prepared by co-precipitation of a nickel-containing material with alumina and promoter compounds such as silica and magnesia. Again, the pressure may be in the range 10-80 bar abs.

Alternatively, the reaction stream may be formed by gasification of coal, biomass or other carbonaceous material with air using gasification apparatus. In such processes the coal, biomass or other carbonaceous material is heated to high temperatures in the absence of a catalyst to form a crude synthesis gas often containing sulphur contaminants such as hydrogen sulphide, which have to be removed. Gasification of carbonaceous feedstock to produce a synthesis gas may be achieved using known fixed bed, fluidised-bed or entrained-flow gasifiers at temperatures in the range 900-1700° C. and pressures up to 90 bar abs. The crude synthesis gas streams require additional treatments known in the art to remove unwanted sulphur and other contaminants.

In a preferred process, the synthesis gas generation stage comprises primary reforming a hydrocarbon, particularly natural gas, in a fired steam reformer to produce a gas stream comprising hydrogen, carbon monoxide, carbon dioxide and steam, and secondary reforming in which the primary reformed gas is further reformed in a secondary reformer using air or oxygen-enriched air to provide a synthesis gas stream comprising hydrogen, carbon oxides and nitrogen.

If desired, one air feed may be provided for both the production of the synthesis gas and the production of the formaldehyde. This offers benefits in the reduction of capital and operating costs when compared to that required for the separate systems utilised in the prior art. In generating synthesis gas on ammonia plants, multiple stages of compression are often used. The air for the methanol oxidation stage may therefore conveniently be taken after the first stage and before the final stage of air compression. This air source therefore removes the need for a separate air compression unit for the formaldehyde stabiliser production unit. Thus in one embodiment, a single source of air is compressed, divided into first and second portions, the first portion provided to a formaldehyde stabiliser production unit and the second portion further compressed and provided to a synthesis gas generation unit. The first portion of compressed air provided to the formaldehyde stabiliser production unit is used to oxidise at least a portion of the methanol. The first portion may be compressed to a pressure in the range 1.1-5 bar abs. The second portion of compressed air fed to the synthesis gas generation unit is used to generate the synthesis gas, for example in a secondary or autothermal reformer. The second portion may be compressed to 10-80 bar abs. If desired, the second portion may also be preheated. The proportion of compressed air fed to the formaldehyde stabiliser production unit may be up to about 20% by volume, preferably in the range 1.5-15% by volume, of the total air fed to the process. The amount or air or oxygen enriched air fed to the secondary reformer may be used to adjust the hydrogen:nitrogen molar ratio in the ammonia synthesis gas, which is often about 3:1. The ratio may be varied if excess nitrogen is included in the secondary reformer and downstream nitrogen adjustment, e.g. by cryogenic cooling and separation or pressure-swing adsorption, and/or hydrogen recovery is used to provide the desired hydrogen:nitrogen ratio. The secondary reformed gas thus comprises nitrogen, hydrogen, steam, carbon dioxide and carbon monoxide and reduced level of methane.

Before recovery of the carbon dioxide, the synthesis gas is subjected in step (b) to one or more stages of water-gas shift to produce a shifted synthesis gas with the desired gas composition. In a water-gas shift stage, a portion of the carbon monoxide in the stream is converted to carbon dioxide. Any suitable catalytic shift conversion reactor and catalyst may be used. If insufficient steam is present, steam may be added to the gas stream before it is subjected to the water-gas shift conversion. The reaction may be depicted as follows;

The reaction may be carried out in one or more stages. The, or each, stage may be the same or different and may be selected from high temperature shift, low temperature shift, medium temperature shift, isothermal shift and sour shift, and is preferably selected from a single stage of high temperature shift, a combination of high temperature shift and low temperature shift, a single stage of medium temperature shift, or a combination of medium temperature shift and low temperature shift.

High temperature shift catalysts may be promoted iron catalysts such as chromia- or alumina-promoted magnetite catalysts. Other high temperature shift catalysts may be used, for example iron/copper/zinc oxide/alumina catalysts, manganese/zinc oxide catalysts or zinc oxide/alumina catalysts. Medium, low temperature and isothermal shift catalysts typically comprise copper, and useful catalysts may comprise varying amounts of copper, zinc oxide and alumina. Alternatively, where sulphur compounds are present in the gas mixture, such as synthesis gas streams obtained by gasification, so-called sour shift catalysts, such as those comprising sulphides of molybdenum and cobalt, are preferred. Such water-gas shift apparatus and catalysts are commercially available.

For high temperature shift catalysts, the temperature in the shift converter may be in the range 300-460° C., for medium temperature shift catalysts the temperature may be in the range 190-300° C. and for low-temperature shift catalysts the temperature may be 185-270° C. For sour shift catalysts, the temperature may be in the range 200-370° C. The flow-rate of synthesis gas containing steam may be such that the gas hourly space velocity (GHSV) through the bed of water-gas shift catalyst in the reactor may be $\geq 6000$ hour$^{-1}$. The pressure may be in the range 10-80 bar abs.

The water-gas shift stage produces a shifted gas. By the term shifted gas we include a partially shifted gas in which the conversion of carbon monoxide to carbon dioxide is incomplete.

In a preferred embodiment, the water-gas shift stage comprises a high temperature shift stage or a medium temperature shift stage or an isothermal shift stage with or without a low temperature shift stage. In another preferred arrangement, the water-gas shift stage comprises a high temperature shift stage to form a partially shifted gas and a low temperature shift stage to form a shifted gas mixture.

Steam present in the shifted gas mixture is condensed in step (c) to form a dried shifted gas, which is fed to the carbon dioxide removal unit. This may be achieved by cooling the shifted gas to below the dew point using one or more heat exchangers fed, for example, with cooling water. The condensate recovered may be fed to a condensate stripping unit or, if desired, be fed to steam generators that produce steam for the synthesis gas generation and/or water-gas shift stages.

A carbon dioxide removal unit is used to recover carbon dioxide from the shifted synthesis gas in step (d). It is located downstream of a water-gas shift stage, and upstream of the methanol synthesis stage. Suitable carbon dioxide removal units function by absorption using a liquid absorbent, i.e. the carbon dioxide is absorbed with or without a chemical reaction by an absorbent liquid. Such liquids are well-known and include for example methanol, glycol, or another liquids suitable for use at low temperatures, such as Rectisol™, Selexol™ units, or by reaction with a suitable reactive absorbent liquids such as aqueous solutions of alkylamines including diethanolamine (DEA), monoethanolamine (MEA), methyldiethanolamine (MDEA), diisopropanolamine (DIPA) and aminoethoxyethanol (Diglycolamine or DGA). Such carbon dioxide removal apparatus and materials are commercially available. The carbon dioxide removal unit comprises an absorption unit comprising one or more absorption vessels to which the dried shifted gas and an absorbent liquid are fed, and an absorbent regeneration unit comprising one or more absorbent regeneration vessels in which a carbon dioxide-laden absorbent liquid is regenerated, typically by heating and/or reducing the pressure. In an absorption vessel, the absorbent liquid and dried shifted gas are contacted, typically in a counter-current manner over one or more packed beds. Carbon dioxide in the dried shifted gas, along with a portion of the hydrogen, is absorbed into the absorbent liquid to produce the carbon dioxide-depleted synthesis gas stream, which is recovered from the absorption vessel. The carbon dioxide-laden absorbent liquid is passed from the absorption unit to one or more regeneration vessels where it is de-gassed to remove carbon dioxide and other absorbed gases. The degassed absorbent liquid may then be fed back to the absorption unit.

In the present invention, the regeneration unit of the carbon dioxide removal unit produces the carbon dioxide-containing gas stream. The carbon dioxide-containing gas stream may suitably be a vent gas stream containing carbon dioxide, hydrogen and other absorbed gases, or may be an essentially pure carbon dioxide stream, or may be a mixture of these. The carbon dioxide-containing gas stream may also comprise steam. Vent gas streams may comprise 10-45 mol % hydrogen, preferably 25-40 mole % hydrogen, more preferably 30-35 mole % hydrogen, whereas the essentially pure carbon dioxide streams may comprise <10 mole % hydrogen, preferably 5 mole % hydrogen.

The regeneration unit may be operated in two or more stages, that is, the de-gassing of the carbon dioxide-laden absorbent liquid may be performed using two or more stages, which are desirably at different pressures that decrease from the inlet to the outlet of the regeneration unit. Thus, the carbon dioxide-containing gas stream may be removed between stages in a single regeneration vessel or between stages operated in two or more regeneration vessels. A vent gas is typically flashed off from the liquid absorbent in a first regeneration vessel or between first and second regeneration vessels as the pressure is reduced. If there are more than two stages, a carbon dioxide-containing gas stream may be recovered at an intermediate pressure between second and third stages and so on, and combined with the vent gas. An essentially pure carbon dioxide stream may be recovered downstream of vent gas recovery in one or more further regeneration vessels.

At least a portion of the carbon dioxide-containing gas stream is recovered, compressed and passed to the methanol synthesis unit.

In one aspect, a vent gas may be recovered from the carbon dioxide removal unit and compressed for use in the methanol synthesis. An additional compressor may be provided for this duty if necessary. Vent gas recovery and use in this way generally should not upset the urea production because conventionally vent gas is sent for use as fuel. Therefore, essentially all of the vent gas recovered from the carbon dioxide removal unit may be provided to the methanol synthesis unit. The amount of vent gas passed to the methanol synthesis unit may be in the range 0.1% to 2.5% by volume of the dried shifted gas fed to the carbon dioxide removal unit.

In another aspect, a portion of an essentially pure carbon dioxide stream recovered from the carbon dioxide removal unit may be compressed for use in the methanol synthesis. Compression of the pure carbon dioxide stream may use the existing compressor used to feed the urea plant. Where a pure carbon dioxide stream is recovered for use in the methanol synthesis unit, the portion of the carbon dioxide used should be small so as not to significantly upset the production of urea. A small reduction in urea production is however generally acceptable when the advantages in providing additional formaldehyde stabiliser are taken into account. The amount of pure carbon dioxide passed to the methanol synthesis unit may be in the range 0.1% to 10% by volume, preferably 0.1% to 5% by volume, more preferably 0.1% to 2.5% by volume of the total pure carbon dioxide separated in the carbon dioxide removal unit.

If the carbon dioxide-containing gas stream is of suitable purity, any compressed gas not sent to the methanol production unit may be fed via the existing compressor to the urea production unit.

Thus, the carbon dioxide removal unit provides a carbon-dioxide-depleted synthesis gas, which may be recovered from the absorption unit, and a carbon dioxide-containing gas stream, which may be recovered from the absorbent regeneration unit, both the absorption unit and the regeneration unit being part of the carbon dioxide removal unit.

The carbon dioxide-containing gas stream is compressed desirably to the inlet pressure of the methanol synthesis reactor in the methanol synthesis unit.

The carbon dioxide-containing gas stream may contain steam, in which case it is preferably cooled to below the dew point to condense the steam as water which may be recovered using a separator. The cooling may be performed using a conventional heat exchanger cooled by e.g. cooling water. Further stages of drying, e.g. with a desiccant may be performed if desired. The cooling and separation of water produces a dry carbon dioxide-containing gas stream which may be compressed. Water removal, or drying, of the carbon dioxide-containing gas stream is desirable to protect the downstream methanol synthesis catalyst, improve the rate of the methanol synthesis reaction and to minimise water in the crude methanol product. Water removal may also improve the performance and reliability of the compression.

If desired, water may also be removed from the carbon dioxide-depleted synthesis gas recovered from the carbon dioxide removal unit by cooling and separation of the condensate as described above. The water removal may be performed on the carbon dioxide-depleted synthesis gas and carbon dioxide-containing gas stream separately, or, on a mixture of the carbon dioxide-depleted synthesis gas and the carbon dioxide-containing gas stream.

The compressed carbon dioxide-containing gas stream is passed to the methanol synthesis unit. It may be passed directly to the methanol synthesis reactor as a separate feed or may be combined with the feed gas to the methanol synthesis unit. The carbon dioxide-containing gas stream contains carbon dioxide and may contain some hydrogen. The carbon dioxide produces additional methanol and the hydrogen in excess of that for methanol synthesis passes to the ammonia production unit where it is a potential source of additional ammonia.

An advantage of using a vent gas stream to augment the methanol production is that this gas is normally used as a fuel and re-use in the process makes more efficient use of this gas. An advantage of using a pure carbon dioxide stream over vent gas is that the existing carbon dioxide recovery technology and equipment may be readily adapted. Therefore, rather than install a new compressor, it is possible to take carbon dioxide from the existing $CO_2$ compressor exit and loop part to the methanol synthesis unit. The higher purity of the $CO_2$ stream also provides advantages in designing and operating the methanol synthesis stage.

Methanol is synthesised in step (e) from the carbon dioxide-depleted synthesis gas and the compressed carbon dioxide-containing gas stream. The synthesis reactions may be depicted as follows:

$$3H_2 + CO_2 \rightleftharpoons CH_3OH + H_2O$$

$$2H_2 + CO \rightleftharpoons CH_3OH$$

Any methanol production technology may be used. Methanol is synthesised in a synthesis unit, which may comprise a methanol converter containing a methanol synthesis catalyst. The process can be on a once-through or a recycle basis in which unreacted product gas, after methanol condensate removal, is mixed with make-up gas comprising hydrogen and carbon oxides in the desired ratio and returned to the methanol reactor. The methanol synthesis, because it is exothermic, may involve cooling by indirect heat exchange surfaces in contact with the reacting gas, or by subdividing the catalyst bed and cooling the gas between the beds by injection of cooler gas, or by indirect heat exchange. However, because the methanol synthesis unit is directed principally to making sufficient formaldehyde for use as a stabiliser, in a preferred arrangement the methanol synthesis unit comprises a single once-through adiabatic methanol synthesis reactor containing a single bed of methanol synthesis catalyst. This arrangement reduces the cost and complexity of the present invention compared to known methanol-ammonia co-production processes.

A crude methanol product comprising methanol, water and trace amounts of impurities such as ethanol may be recovered by cooling of the product gas stream recovered from the methanol reactor to below the dew point, e.g. with cooling water. If desired, liquid ammonia may be used in a further cooling stage. Alternatively, or in addition, methanol may be recovered by scrubbing the product gas with water. Water scrubbing is particularly suitable in the present invention.

Any methanol synthesis catalyst may be used, but preferably it is based on a promoted or un-promoted copper/zinc oxide/alumina composition, for example those having a copper content in the range 50-70% wt. Promoters include oxides of Mg, Cr, Mn, V, Ti, Zr, Ta, Mo, W, Si and rare earths. In the catalyst, the zinc oxide content may be in the range 20-90% wt, and the one or more oxidic promoter compounds, if present, may be present in an amount in the range 0.01-10% wt. Magnesium compounds are preferred promoters and the catalyst preferably contains magnesium in an amount 1-5% wt, expressed as MgO. The synthesis gas may be passed over the catalyst at a temperature in the range 200-320° C., and at a pressure in the range 20-250 bar abs, preferably 20-120 bar abs, more preferably 20-50 bar abs, and a space velocity in the range 500-20000 $h^{-1}$. Because the aim of the process is not to maximise methanol production, the inlet temperature of the methanol synthesis stage may be lower, e.g. 200-270° C. thus extending the catalyst lifetime by reducing sintering of the active copper sites.

In the present process, a single stage of methanol synthesis is generally sufficient. Nevertheless, if desired, the methanol synthesis may be part of a multiple stage synthesis process where the product gas, with or without condensate removal, is fed to one or more further methanol synthesis reactors, which may contain the same or different methanol synthesis catalyst. Such methanol production apparatus and catalysts are commercially available. A purge gas stream may be removed to prevent the undesirable build-up of inert/unreactive gases. If desired methanol may also be synthesised from this purge gas, or hydrogen recovered from it to adjust the stoichiometry of the feed gas or to generate power. In the process, preferably all of the recovered methanol is oxidised to produce formaldehyde.

The crude methanol contains water and other impurities that may be separated from the product methanol by one or more stages of distillation. The formaldehyde stabiliser production unit may use purified methanol as the feed or a crude methanol as the feed. By "crude methanol" we include the direct product of the methanol synthesis reactor and a methanol product in which the water content has been adjusted, e.g. by a single purification step, to the range 5-20% by weight so that the formaldehyde stabiliser products are produced efficiently at suitable concentrations. This makes it possible to send crude methanol directly to the formaldehyde plant without the need for multiple distillation steps. Using crude methanol saves both capital cost on distillation columns and associated equipment, as well as the operating cost of this equipment, resulting in a significant benefit.

The crude methanol may be sent for storage in a suitable storage tank. Alternatively, the crude methanol may be subjected to one or more purification stages, including a de-gassing stage, in a methanol purification unit prior to feeding it to the oxidation reactor. The de-gassing stage or any distillation stages may be provided by distillation columns heated using heat recovered from the oxidation reactor or elsewhere in the process. In particular, the degassing stage may be heated using steam generated by the oxidation stage. This simplification of the methanol purification offers significant savings in capital and operating costs for the process.

The unreacted gas stream recovered from the methanol synthesis unit after separation of the crude methanol stream is the methanol synthesis off-gas. It comprises nitrogen, hydrogen, and small amounts of methane, argon, carbon monoxide and carbon dioxide.

Methanol is oxidised to formaldehyde in step (f). Any formaldehyde production technology using air as the oxidant may be used. The formaldehyde is synthesised in a formaldehyde stabiliser production unit, which may comprise an oxidation reactor containing an oxidation catalyst. The oxidation catalyst may be provided as a fixed bed or within externally-cooled tubes disposed within the reactor. A compressed air source, which may be from the single source as described above, is used in the formaldehyde stabiliser production unit. The air may be at a temperature in the range of 10-50° C. The air and methanol may be passed to the reactor containing an oxidation catalyst in which the methanol is oxidised. Air is preferably provided at 1.1-5 bar abs, e.g. from a first stage of compression of the air fed to the process.

Production of formaldehyde from methanol and oxygen may be performed either in a silver- or a metal oxide catalysed process operated under methanol-rich or methanol-lean conditions, respectively. Hence the oxidation catalyst may be selected from either a silver catalyst or a metal oxide catalyst, the latter preferably comprising a mixture of iron and molybdenum oxides. Vanadium oxide catalysts may also be used. In the metal oxide process, the principal reaction is the oxidation of the methanol to formaldehyde;

$$2CH_3OH + O_2 \rightarrow 2CH_2O + 2H_2O$$

Over silver catalysts, in addition to the above oxidation reaction, methanol is also dehydrogenated in the principal reaction;

$$CH_3OH \rightarrow CH_2O + H_2$$

In the metal oxide process, formaldehyde is produced in multi-tube reactors. Typically, a reactor comprises 10-30,000 tubes containing catalyst pellets or extrudates and cooled by oil or by molten salts as heat transfer fluid. Since the reaction is highly exothermic ($\Delta H = -156$ kJ/mol), isothermal conditions are difficult to obtain and consequently a hotspot may be formed within the reaction zone. In order to limit the hot spot temperature, at the first part of the reactor the catalyst can be diluted with inert pellets or extrudates. The catalyst used in the oxide process is preferably a mixture of iron molybdate $Fe_2(MoO_4)_3$ and molybdenum trioxide $MoO_3$ with a Mo:Fe atomic ratio between 2 and 3. The plant yield is high (88-94%) and neither molybdenum nor iron are toxic, which is favourable considering both environmental and human health aspects.

Air is preferably used at levels to maintain the oxygen content at the inlet of the reactor below the explosive limit. The feed gas may therefore comprise 6.5 vol % methanol for a once-through reactor or about 8-11 vol % methanol where there is recirculation. The oxidation reactor may be operated adiabatically or isothermally, where the heat of reaction can be used to generate steam. The inlet temperature to the oxidation reactor is typically in the range 80-270° C., with iron-based catalytic processes operating up to 400° C. and silver-based processes up to 650° C.

A single passage through the oxidation reactor can result in high yields of formaldehyde, or if desired it is possible to recycle unreacted gases, which comprise mainly of nitrogen, to the reactor inlet to maintain a low oxygen concentration. Due to the scale required in the present process, the formaldehyde production stage may be operated without recycle of oxidised gas to the inlet of the oxidation reactor as this removes the need for a recycle compressor and hence offers further savings.

An absorption tower may be used to extract the formaldehyde product from the oxidised gas mixture into either water to produce aqueous formaldehyde solution, or a urea solution to produce a urea-formaldehyde concentrate (UFC). The absorption tower may contain a selection of packing, trays and other features to promote the absorption, and cooling water may be used to provide the product at a temperature in the range 20-100° C. The absorption stage typically runs at a slightly lower pressure than the reactor.

In the present process, products made from the formaldehyde are used to stabilise urea. The formaldehyde stabiliser production unit may be used to produce an aqueous formaldehyde solution (formalin) or a urea-formaldehyde concentrate (UFC). Urea formaldehyde concentrate that may be used typically comprises a mixture of about 60% wt formaldehyde, about 25% wt urea and the balance about 15% water. Such a product may be termed "UFC85". Other UFC products may also be used, e.g. UFC80. Other formaldehyde products may also be produced. Excess formaldehyde products may be recovered and sold.

The formaldehyde stabiliser production unit generates a stabiliser unit vent gas which may be passed to a stabiliser unit vent gas treatment unit such as an emission control unit or emission control system (ECS) and discharged to atmosphere. An emission control unit or system may comprise a catalytic combustor that reacts any carbon monoxide, methanol, formaldehyde and dimethyl ether in the stabiliser unit vent gas with oxygen. The gas emitted from an ECS, i.e. an ECS effluent, may comprise carbon dioxide, steam and nitrogen and therefore may be recycled, preferably after suitable compression, to one or more stages of the process. Thus, the ECS effluent may be passed to the carbon dioxide-removal stage where steam and carbon dioxide may be recovered, to provide additional nitrogen in the synthesis gas. Alternatively, the ECS effluent may be provided to the methanol synthesis stage where the carbon dioxide may be reacted with hydrogen in the synthesis gas to produce additional methanol. Alternatively, the ECS effluent may be fed to the urea production unit to provide carbon dioxide for additional urea production.

In another embodiment, the stabiliser unit vent gas treatment unit may comprise a gas-liquid separator that separates the nitrogen-rich off-gas from liquid methanol, which may be recycled to the oxidation reactor directly or after one or more stages of purification. The nitrogen-rich gas separated in the separator may be compressed and passed to the ammonia synthesis stage.

Alternatively, the stabiliser unit vent gas may be recycled directly to the process, i.e. the stabiliser unit vent gas treatment system may be omitted.

In one embodiment, the stabiliser unit vent gas is recycled directly to the synthesis gas generation unit as a fuel gas so that the organic contaminants present in the stabiliser unit vent gas may be combusted to generate energy. The stabiliser unit vent gas may, for example, be recycled directly to the fuel gas stream of a primary reformer or may be fed to a furnace for steam generation. In this way, a stabiliser unit vent gas treatment unit is not required, which offer considerable savings. Alternatively, the stabiliser unit vent gas may be combined with a hydrocarbon feedstock fed to the synthesis gas generation unit. Alternatively, the stabiliser unit vent gas may be recycled directly to the carbon dioxide removal stage so that the carbon dioxide and water vapour present in the stabiliser unit vent gas may be captured. Organic contaminants such as methanol, formaldehyde and dimethyl ether may also be captured, e.g. using a PSA unit. Alternatively, the stabiliser unit vent gas maybe recycled directly to the methanol synthesis stage. Direct recycling is simpler and is preferred. With direct recycling, the by-products will be limited by equilibrium across the methanol synthesis catalyst and so will not accumulate in any recycle loop. The nitrogen is also recovered without the need for catalytic combustion or intensive pressurisation. The stabiliser unit vent gas may be recycled directly to one, two or more of these alternatives.

The formaldehyde stabiliser production unit may also produce an aqueous waste stream, for example a condensate recovered as a by-product of the methanol oxidation. This condensate may contain organic compounds such as methanol, formaldehyde and dimethyl ether and therefore provide a potential source of hydrocarbon for the process. In one embodiment, the process condensate is recycled to the synthesis gas generation stage where it is used to generate steam for use in steam reforming. The steam may be formed in a conventional boiler and added to the hydrocarbon feed or may, preferably, be generated in a saturator to which the aqueous effluent and hydrocarbon are fed.

In the methanation stage (g), residual carbon monoxide and carbon dioxide in the methanol synthesis off-gas stream is converted to methane in the methanator. Any suitable arrangement for the methanator may be used. Thus, the methanator may be operated adiabatically or isothermally. One or more methanators may be used. A nickel-based methanation catalyst may be used. For example, in a single methanation stage, the gas from the methanol synthesis stage may be fed at an inlet temperature in the range 200-400° C., preferably 325-375° C., to a fixed bed of pelleted nickel-containing methanation catalyst. Higher inlet temperatures are useful to decompose any methanol in the feed gas. Such catalysts are typically pelleted compositions, comprising 20-40% wt nickel. Such methanation apparatus and catalysts are commercially available. The pressure for methanation may be in the range 10-80 bar abs or higher up to 250 bar abs. Steam is formed as a by-product of methanation. The steam is desirably removed using conventional means such as cooling and separation of condensate. An ammonia synthesis gas stream may be recovered from the methanation and drying stage. Such methanation apparatus and catalysts are commercially available.

The methanated gas stream may be fed to the ammonia production unit as the ammonia synthesis gas. The hydrogen:nitrogen molar ratio of the methanated gas stream may need to be adjusted, for example by addition of nitrogen from a suitable source, or by removal of nitrogen, to provide the ammonia synthesis gas. Nitrogen, if added, may be provided from any source, for example from an air separation unit (ASU) and the adjustment may be performed by direct addition of nitrogen to the methanated gas stream. Nitrogen, if removed, may be removed from the synthesis gas by cryogenic cooling to recover liquid nitrogen or may be achieved using pressure-swing adsorption on a suitable adsorbent. Such cryogenic and pressure-swing absorption apparatus and adsorbents are commercially available. The adjusted gas mixture may then be passed to the ammonia synthesis unit as the ammonia synthesis gas.

Ammonia is synthesised in step (h). The ammonia synthesis gas may be compressed to the ammonia synthesis pressure and passed to an ammonia production unit. The ammonia production unit comprises an ammonia converter containing an ammonia synthesis catalyst. The nitrogen and hydrogen react together over the catalyst to form the ammonia product. Ammonia synthesis catalysts are typically iron based but other ammonia synthesis catalysts may be used. The reactor may operate adiabatically or may be operated isothermally. The catalyst beds may be axial and/or radial flow and one or more beds may be provided within a single converter vessel. The conversion over the catalyst is generally incomplete and so the synthesis gas is typically passed to a loop containing a partially reacted gas mixture recovered from the ammonia converter and the resulting mixture fed to the catalyst. The synthesis gas mixture fed to the loop may have a hydrogen:nitrogen ratio of 2.2-3.2, but is often about 3.0, e.g. 2.9-3.1. In the ammonia production unit, the hydrogen/nitrogen mixture may be passed over the ammonia synthesis catalyst at high pressure, e.g. in the range 80-350 bar abs, preferably 150-350 bar abs, and a temperature in the range 300-540° C., preferably 350-520° C.

A purge gas stream containing methane and hydrogen may be taken from the ammonia synthesis loop and fed to the synthesis gas generation step or used as a fuel.

Compression of the synthesis gas is preferably effected in multiple stages, with a first and a second stage performed before the methanol synthesis to achieve e.g. 50-100 barg, preferably 80-100 barg, and a third stage after methanation to achieve a higher pressure, e.g. 150-250 barg, before the ammonia synthesis. Thus, methanol synthesis may usefully be provided between the second and third stages of compression, with the methanator downstream of methanol synthesis and upstream of the third stage of compression. Alternatively, the methanol synthesis may usefully be provided upstream of the first stage of compression.

Urea is produced in step (i) by reacting ammonia from step (h) with carbon dioxide recovered from step (d). Typically, only a portion of the ammonia produced in step (h) will be used to produce urea, which is limited by the amount of carbon dioxide recovered in step (d). The excess ammonia may be recovered and used to make nitric acid, ammonium nitrate or ammonia products for sale. Any urea production technology may be used. For example, ammonia and carbon dioxide may be combined in a first reactor in the range 140-200° C. and 120-220 bar abs to form ammonium carbamate as follows;

$$NH_3 + CO_2 \rightleftharpoons NH_2COONH_4$$

The ammonium carbamate is then dehydrated in a further reactor to form urea;

$$NH_2COONH_4 \rightleftharpoons NH_2CONH_2 + H_2O$$

The high pressure favours ammonium carbamate formation and the high temperature favours the dehydration, so the resultant mixture contains all the above components. Unreacted carbamate is therefore generally decomposed back to ammonia and carbon dioxide, which may then be recycled to the reactor. The carbon dioxide readily dissolves in the water from the dehydration, which if recycled suppresses the equilibria and so the system may be run with excess ammonia to minimise this recycle. The decomposition and subsequent recycling can be carried out in one or more successive stages at decreasing pressures to minimise the ultimate concentration of ammonium carbamate dissolved in the urea solution. An alternative process arrangement uses the fresh carbon dioxide gas to strip unreacted ammonia and carbon dioxide from the ammonium carbamate and urea solution at the same pressure as the reactor. Further unreacted material is recycled from lower pressure stages as ammonium carbamate solution. Such urea production apparatus is commercially available.

A formaldehyde-stabilised urea is produced in step (j) by mixing urea produced in step (i) and a stabiliser prepared using formaldehyde produced by the formaldehyde stabiliser production unit in step (f). The stabiliser may be any formaldehyde-containing stabiliser; including aqueous formaldehyde and an aqueous urea-formaldehyde concentrate. Aqueous formaldehyde and urea formaldehyde concentrate may be prepared directly in the formaldehyde stabiliser production unit. Formaldehyde, either as a concentrated solution or as a combined solution of urea and formaldehyde may be added as a stabiliser to molten urea prior to forming into either pills or granules. This reduces the tendency of the urea to absorb moisture and increases the hardness of the surface of the solid particles, preventing both caking (bonding of adjacent particles) and dusting (abrasion of adjacent particles). This maintains the free-flowing nature of the product, prevents loss of material through dust and enhances the stability during long term storage. If urea is available, then it is preferable to use a urea formaldehyde solution because this minimises the amount of water being added to the molten urea. Such formaldehyde-stabilised urea production apparatus is commercially available.

The present invention will now be described by way of example with reference to the accompanying drawings in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Figure 1:
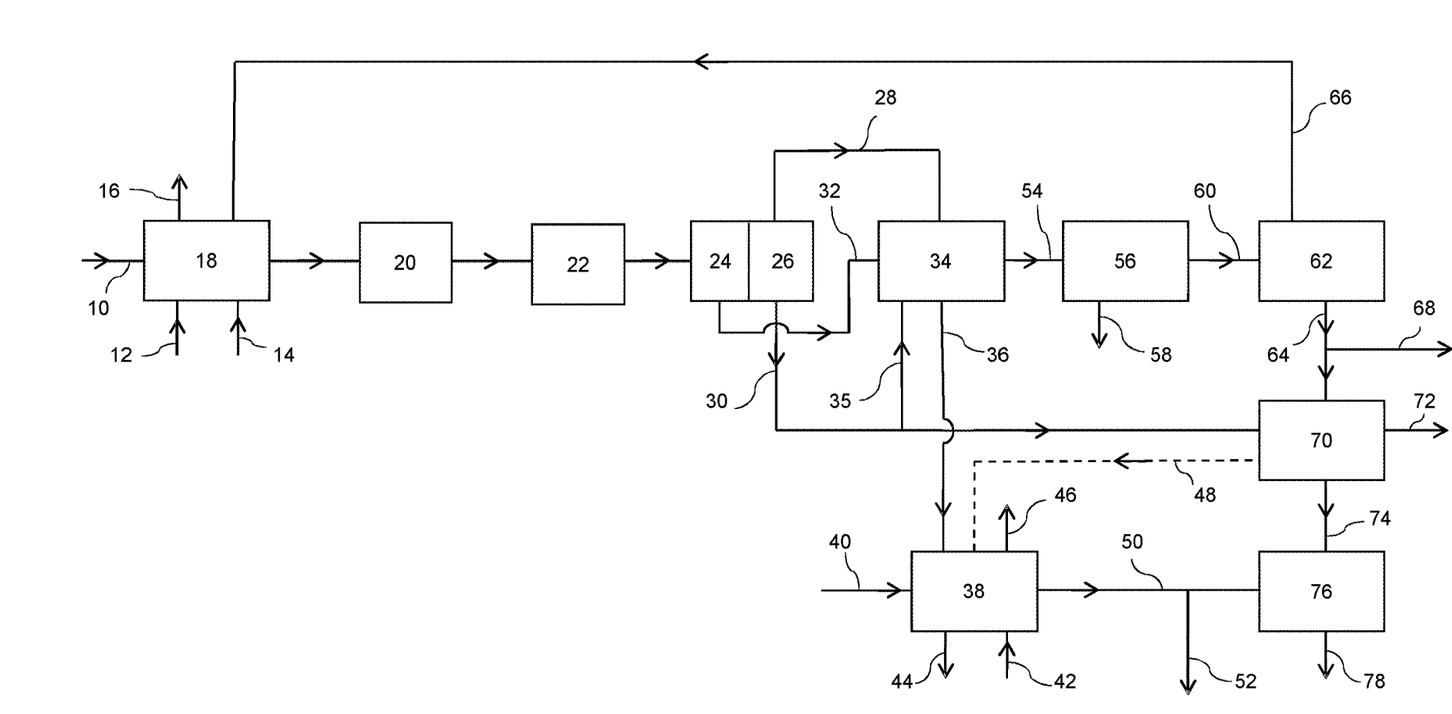
FIG. 1 is a schematic representation of a process according to a first aspect of the present invention.

In FIG. 1, a natural gas stream 10, steam 12 and an air stream 14 are fed to a synthesis gas generation unit 18 comprising a primary reformer and secondary reformer. The natural gas is primary reformed with steam in externally-heated catalyst filled tubes in the primary reformer and the primary reformed gas subjected to secondary reforming in the secondary reformer with the air to generate a raw synthesis gas comprising nitrogen, hydrogen, carbon dioxide, carbon monoxide and steam. A portion of the natural gas may by-pass the primary reformer and be fed along with the primary reformed gas to the secondary reformer. A flue gas 16 is discharged from the primary reformer. The steam to carbon monoxide ratio of the raw synthesis gas may be adjusted by steam addition if necessary and the gas subjected to water-gas shift in a high temperature shift reactor 20 containing a high temperature shift catalyst and then a low temperature shift reactor 22 containing a low temperature shift catalyst. The water-gas shift reaction increases the hydrogen and carbon dioxide contents and the steam and carbon monoxide contents are decreased. The shifted synthesis gas is fed to a carbon dioxide removal unit comprising an absorption unit 24 and a regeneration unit 26. The absorption unit 24 comprises a single absorption vessel in which the shifted synthesis gas is contacted with a liquid absorbent. The liquid absorbent absorbs carbon dioxide to produce a carbon dioxide-depleted synthesis gas 32 comprising hydrogen, carbon monoxide and nitrogen. A carbon dioxide-laden absorbent liquid is fed from the absorption unit 24 to a regeneration unit 26 comprising an absorbent regeneration vessel operating in two stages, with the first stage operating at a higher pressure than the second stage. A vent gas 28 containing carbon dioxide and hydrogen is recovered from the regeneration unit 26 between the first stage and the second stage. A carbon dioxide stream 30 is recovered from the second stage of the regeneration unit 26 for further use. If desired, the vent gas 28 may be cooled to below the dew point in a heat exchanger and the condensate separated in a separator to provide a dry vent gas. The vent gas 28 (or dry vent gas) is compressed by a compressor (not shown) to form a compressed vent gas. The compressed vent gas 28 and the carbon dioxide-depleted synthesis gas 32 recovered from the absorption unit 24 are passed to a methanol synthesis unit 34 comprising a methanol converter containing a bed of methanol synthesis catalyst. Alternatively, or in addition, a portion of the recovered carbon dioxide stream 30 may be dried if necessary to remove water, compressed and fed to the methanol synthesis unit, via line 35. Although separate streams are depicted, it may be convenient to combine these streams upstream of the methanol synthesis unit. If desired, upstream of the methanol synthesis unit 34, water in the carbon dioxide-depleted synthesis gas 32 may also be removed by cooling and separation of the condensate. The vent gas 28, and/or carbon dioxide stream 35 and carbon dioxide-depleted synthesis gas 32 may be heated if necessary before feeding them to the methanol synthesis unit 34. Methanol is synthesised in a single converter on a once-through basis and separated from the product gas mixture. A crude methanol product is recovered from the methanol synthesis unit 34 by line 36 and passed to a stabiliser production unit 38 comprising an oxidation reactor containing an oxidation catalyst. An air source 40 is fed to the oxidation reactor where it is reacted with the methanol to produce formaldehyde. The oxidation reactor is operated in a loop with a portion of the reacted gas fed to the inlet of the reactor. The formaldehyde stabiliser production unit is fed with cooling water 42 and generates a steam stream 44 and a stabiliser unit vent gas 46. The formaldehyde produced in the oxidation reactor is recovered in an absorption tower which may be fed with water and optionally urea via line 48 such that either aqueous formaldehyde or a urea-formaldehyde concentrate (UFC) product stream 50 may be recovered from the stabiliser production unit 38 for further use. A portion 52 of the stabiliser product stream 50 can be taken for use in, for example, a separate urea-stabilisation plant or for sale, if the flow of stabiliser produced is in excess of that required for the associated urea plant.

A methanol synthesis off-gas stream 54 comprising hydrogen, nitrogen and unreacted carbon monoxide recovered from the methanol synthesis unit 34 is passed to a methanation unit 56 comprising a methanation reactor containing a bed of methanation catalyst. Carbon oxides remaining in the off-gas 54 are converted to methane and water in the methanation reactor. Water is recovered from the methanation unit 56 by line 58. The methanated off-gas is an ammonia synthesis gas comprising nitrogen and hydrogen and a small amount of methane. The ammonia synthesis gas is passed from the methanation unit 56 by line 60 to an ammonia synthesis unit 62 comprising an ammonia converter containing one or more beds of ammonia synthesis catalyst. The ammonia converter is operated in a loop with a portion of the reacted gas fed to the inlet of the converter. Ammonia is produced in the converter and recovered from the ammonia synthesis unit 62 by line 64. A purge gas stream 66 comprising methane and unreacted hydrogen and nitrogen is recovered from the ammonia synthesis unit 62 and provided to the synthesis gas generation unit 18 as fuel. A portion 68 of the ammonia is separated from the product stream 64. The remaining ammonia is passed to a urea synthesis unit 70 where it is reacted with a purified carbon dioxide stream provided by stream 30 to produce a urea stream and water. Water is recovered from the urea synthesis unit 70 by line 72. The urea stream is passed by line 74 to a stabilisation unit 76 comprising a stabilisation vessel where it is treated with aqueous formaldehyde or a urea formaldehyde concentrate provided by line 50 to form a stabilised urea product. The stabilised urea product is recovered from the stabilisation unit 76 by line 78.

The invention will now be described with reference to the following examples in accordance with the process of FIG. 1.

Example 1

A formaldehyde-stabilised urea process was modelled based on a shifted synthesis gas having a composition as follows;

| | |
|---|---|
| $CO_2$ | 13.0 mole % |
| CO | 0.1 |
| $H_2$ | 44.4 |
| $N_2$ | 14.9 |
| Ar | 0.2 |
| $CH_4$ | 0.2 |
| $H_2O$ | 27.2 |

The shifted synthesis gas (162479 kg/hr) was cooled, condensate removed and fed to a $CO_2$ removal unit comprising an absorption vessel fed with MDEA and a regeneration vessel in which the $CO_2$-laden absorbent was regenerated. The absorption vessel produced 54568 kg/h of a $CO_2$-depleted synthesis gas for methanol synthesis having the following composition;

| | |
|---|---|
| $CO_2$ | 0.1 mole % |
| CO | 0.2 |
| $H_2$ | 73.6 |
| $N_2$ | 24.6 |
| Ar | 0.3 |
| $CH_4$ | 0.3 |
| $H_2O$ | 0.9 |

The regeneration vessel produced 1797 hg/hr of a vent gas having the following composition;

| | |
|---|---|
| $CO_2$ | 55.0 mole % |
| CO | 0.2 |
| $H_2$ | 33.0 |
| $N_2$ | 6.0 |
| Ar | 0.0 |
| $CH_4$ | 0.4 |
| $H_2O$ | 5.4 |

The vent gas was compressed from its pressure of 2.5 bar abs to 29.2 bar abs.

The $CO_2$-depleted synthesis gas and the compressed vent gas were provided to a methanol synthesis reactor operating at 200° C. The additional methanol production by including the vent gas was calculated to be 11.6 tonnes/day. The additional methanol is able to provide additional formaldehyde stabiliser.

Example 2

A urea plant (taking ammonia from more than one facility) was modelled based on the shifted synthesis gas for one of the ammonia facilities, having a composition as follows;

| | |
|---|---|
| $CO_2$ | 12.7 mole % |
| CO | 0.2 |
| $H_2$ | 42.9 |
| $N_2$ | 15.1 |
| Ar | 0.2 |
| $CH_4$ | 0.6 |
| $H_2O$ | 28.3 |

The shifted synthesis gas (282074 kg/hr) was cooled, condensate removed and fed to a $CO_2$ removal unit comprising an absorption vessel and a regeneration vessel in which the $CO_2$-laden absorbent was regenerated. The absorption vessel produced 96214 kg/hr of a $CO_2$-depleted synthesis gas having the following composition;

| | |
|---|---|
| $CO_2$ | 0.2 mole % |
| CO | 0.3 |
| $H_2$ | 71.9 |
| $N_2$ | 25.3 |
| Ar | 0.3 |
| $CH_4$ | 1.0 |
| $H_2O$ | 1.0 |

The $CO_2$-depleted synthesis gas was found to contain insufficient carbon oxides to produce enough methanol, and so UFC-85 stabiliser, to meet the demands of the urea plant. According to the present invention, 1460 kg/hr purified carbon dioxide (about 1.5% by volume of the overall carbon dioxide recovered) was combined with the carbon dioxide-depleted synthesis gas, resulting in a synthesis gas fed to the methanol synthesis unit having the following composition;

| | |
|---|---|
| $CO_2$ | 0.5 mole % |
| CO | 0.3 |
| $H_2$ | 71.7 |
| $N_2$ | 25.2 |
| Ar | 0.3 |
| $CH_4$ | 1.0 |
| $H_2O$ | 1.0 |

The synthesis gas was provided to a methanol synthesis reactor at 215° C. The additional methanol production by including the vent gas was calculated to be 9 tonnes/day—sufficient to make enough UFC-85 stabiliser to feed the urea plant. There is a slight but acceptable reduction in the ammonia production (1.3% on a mass basis).

The invention claimed is:

1. A process for the production of formaldehyde-stabilized urea comprising the steps of:
   (a) generating a synthesis gas comprising hydrogen, nitrogen, carbon monoxide, carbon dioxide and steam in a synthesis gas generation unit;
   (b) subjecting the synthesis gas to one or more stages of water-gas shift in one or more water-gas shift reactors to form a shifted gas;
   (c) cooling the shifted gas to below the dew point and recovering condensate to form a dried shifted gas;
   (d) recovering carbon dioxide from the dried shifted gas in a carbon dioxide removal unit to form a recovered carbon dioxide-containing gas stream and a carbon dioxide-depleted synthesis gas;
   wherein the carbon dioxide removal unit operates by means of absorption using a liquid absorbent and comprises an absorbent regeneration unit, wherein the process includes recovering the carbon dioxide-containing gas stream from the absorbent regeneration unit, compressing a first portion of the recovered carbon dioxide-containing gas stream to form a compressed carbon dioxide-containing gas stream and passing the compressed carbon dioxide-containing gas stream to a methanol synthesis unit and separately passing a second portion of the recovered carbon dioxide-containing gas stream to a urea production unit;
   (e) synthesizing methanol from the carbon dioxide-depleted synthesis gas and the compressed carbon dioxide-containing gas stream in the methanol synthesis unit and recovering the methanol and a methanol synthesis off-gas comprising nitrogen, hydrogen and residual carbon monoxide;
   (f) subjecting at least a portion of the recovered methanol to oxidation with air to form formaldehyde in a stabilizer production unit;
   (g) subjecting the methanol synthesis off-gas to methanation in a methanation reactor containing a methanation catalyst to form an ammonia synthesis gas;
   (h) synthesizing ammonia from the ammonia synthesis gas in an ammonia production unit and recovering the ammonia;
   (i) reacting a portion of the ammonia and the second portion of the recovered carbon dioxide stream in the urea production unit to form a urea stream; and
   (j) stabilizing the urea by mixing the urea stream and a stabilizer prepared using the formaldehyde produced in the stabilizer production unit.

2. The process of claim 1, wherein the synthesis gas generation stage comprises steam reforming of a hydrocarbon or the gasification of a carbonaceous feedstock.

3. The process of claim 1, wherein the synthesis gas generation stage comprises primary reforming in a fired or gas-heated steam reformer and secondary reforming in a secondary reformer with air or oxygen-enriched air.

4. The process of claim 1, wherein the one or more stages of water-gas shift comprise one or more stages of high temperature shift, low temperature shift, medium temperature shift, isothermal shift and sour shift.

5. The process of claim 1, wherein carbon dioxide removal unit comprises an absorption unit comprising one or more absorption vessels to which the dried shifted gas and an absorbent liquid are fed, and an absorbent regeneration unit comprising one or more absorbent regeneration vessels in which a carbon dioxide-laden absorbent liquid is regenerated by heating and/or reducing the pressure, to produce the carbon dioxide-containing gas stream.

6. The process of claim 1, wherein the carbon dioxide-containing gas stream comprises a vent gas stream containing carbon dioxide, hydrogen and other absorbed gases, an essentially pure carbon dioxide stream, or a mixture of these.

7. The process of claim 6, wherein the vent gas stream comprises 10 mole % to 45 mole % hydrogen.

8. The process of claim 6, wherein the vent gas stream contains essentially pure carbon dioxide stream comprising less than 10 mole % hydrogen.

9. The process of claim 6, wherein the amount of vent gas passed to the methanol synthesis unit is in the range of from 0.1% to 2.5% by volume of the dried shifted gas fed to the carbon dioxide removal unit.

10. The process of claim 6, wherein the amount of pure carbon dioxide passed to the methanol synthesis unit is in the range of from 0.1% to 10% by volume.

11. The process of claim 1, wherein the carbon dioxide-containing gas stream further comprises steam and before compression, the carbon dioxide-containing gas stream is cooled to below the dew point to condense the steam as water which is recovered using a separator to produce a dry carbon dioxide-containing gas stream.

12. The process of claim 1, wherein the methanol synthesis unit is operated on a once-through basis, or on a recycle basis in which unreacted gases, after methanol removal, are returned to the methanol synthesis reactor in a loop.

13. The process of claim 1, wherein the methanol synthesis is operated in a single stage at an inlet temperature to the catalyst in the range of from 200° C. to 320° C.

14. The process of claim 1, wherein a crude methanol product recovered from the methanol synthesis stage is fed to the oxidation reactor.

15. The process of claim 1, wherein the formaldehyde stabilizer production unit generates a stabilizer unit vent gas which is recycled to the process, either directly or after one or more stages of vent gas treatment in a vent-gas treatment unit.

16. The process of claim 4, wherein the one or more stages of water-gas shift comprise a single stage of high temperature shift, a combination of high temperature shift and low temperature shift, a single stage of medium temperature shift, or a combination of medium temperature shift and low temperature shift.

17. The process of claim 7, wherein the vent gas stream comprises 25 mole % to 40 mole % hydrogen.

18. The process of claim 8, wherein the essentially pure carbon dioxide stream comprises 5 mole % or less hydrogen.

19. The process of claim 10, wherein the amount of pure carbon dioxide passed to the methanol synthesis unit is in the range 0.1% to 5% by volume of the total pure carbon dioxide separated in the carbon dioxide removal unit.

20. The process of claim 13, wherein the methanol synthesis is operated in a single stage at an inlet temperature to the catalyst in the range of from 200° C. to 270° C.

* * * * *